(12) United States Patent
Peralta Uroz et al.

(10) Patent No.: US 8,748,086 B2
(45) Date of Patent: Jun. 10, 2014

(54) AQUEOUS SOLUTION FOR THE PRESERVATION OF TISSUES AND ORGANS

(75) Inventors: Carmen Peralta Uroz, Barcelona (ES); Joan Rosselló-Catafau, Barcelona (ES); Ismail Ben Mosbah, Cornellá de Llobregat (ES); Ramon Bartrons Bach, Barcelona (ES)

(73) Assignees: Universidad de Barcelona, Barcelona (ES); Consejo Superior de Investigaciones Científicas, Madrid (ES); Institut d'Investigacions Biomèdiques August Pi I Sunyer, Barcelona (ES)

( * ) Notice: Subject to any disclaimer, the term of this patent is extended or adjusted under 35 U.S.C. 154(b) by 507 days.

(21) Appl. No.: 12/993,292

(22) PCT Filed: May 18, 2009
(Under 37 CFR 1.47)

(86) PCT No.: PCT/ES2009/000267
§ 371 (c)(1),
(2), (4) Date: Jul. 26, 2011

(87) PCT Pub. No.: WO2009/141470
PCT Pub. Date: Nov. 26, 2009

(65) Prior Publication Data
US 2013/0059285 A1    Mar. 7, 2013

(30) Foreign Application Priority Data
May 19, 2008    (ES) .................................. 200801560

(51) Int. Cl.
*A01N 1/00*    (2006.01)
*A01N 1/02*    (2006.01)
*C12N 5/07*    (2010.01)

(52) U.S. Cl.
USPC ............................ 435/1.1; 435/325; 435/374

(58) Field of Classification Search
USPC ....................................................... 435/1.1
See application file for complete search history.

(56) References Cited
U.S. PATENT DOCUMENTS
2004/0242565 A1 * 12/2004 Toshima et al. ............... 514/218

OTHER PUBLICATIONS

Franco-Gou et al. "New preservation strategies for preventing liver grafts against cold ischemia reperfusion injury", Hepatology 22: 1120-1126, 2007.*
Papezikova, I. et al.; "SFRBM's 14th Annual Meeting: Program and Abstracts," Free Radical Biology and Medicine, 2007, 43.
Laurens, M. et al.; "Warm Ischemia-Reperfusion Injury Is Decreased by Tacrolimus in Steatotic Rat Liver," Liver Transplantation, 2006, pp. 217-225, vol. 12.
Ben-Mosbah, I. et al.; "Trimetazidine: Is it a promising drug for use in steatotic grafts?" World J. Gastroenterol, 2006, pp. 908-914, vol. 12.
Yue, T. et al.; "Carvedilol inhibits activation of stress-activated protein kinase and reduces reperfusion injury in perfused rabbit heart," European Journal of Pharmacology, 1998, pp. 61-65, vol. 345.
Zoppo, A. et al.; "Trimetazidine Counteracts Tacrolimus Nephrotoxicity in a Hypertensive Liver Transplant Patent," Transplantation, 1999, p. 1211, vol. 68.
Singh, D. et al.; "Carvedilol and trimetazidine attenuates ferric nitrilotriacetate-induced oxidative renal injury in rat," Toxicology, 2003, pp. 143-151, vol. 191.
El-Wahsh M. et al, "Liver graft preservation: an overview," Hepatobiliary Pancreatic Diseases International, 2007, pp. 12-16, vol. 6.
Ben-Mosbah I. et al.; "Preservation of Steatotic Livers in IGL-1 Solution," Liver Transplantation, 2006, pp. 1215-1223, vol. 12.
Cargnoni A. et al.; "Reduction of oxidative stress by carvedilol: role in maintenance of ischaemic myocardium viability," Cardiovascular Research, 2000, pp. 556-566, vol. 47.
Feng X.-N. et al.; "Current status and perspective of liver preservation solutions," Hepatobiliary and Pancreatic Diseases International, 2006, pp. 490-494, vol. 15.
Hauet T. et al.; "Trimetazidine Reduces Renal Dysfunction by Limiting the Cold Ischemia/Reperfusion Injury in Autotransplanted Pig Kidneys," Jounal of the American Society of Nephrology, 2000, pp. 138-148, vol. 11.
Ben-Mosbah I. et al.; "Addition of Adenosine Monophosphate-Activated Protein Kinase Activators to University of Wisconsin Solution: A Way of Protecting Rat Steatotic Livers," Liver Transplantation, 2007, pp. 410-425, vol. 13.
Ben-Mosbah I. et al.; "Additoin of Carvedilol to University Wisconsin Solution Improves Rat Steatotic and Nonsteatotic Liver Preservation," Liver Transplantation, 2010, pp. 163-171, vol. 16.

* cited by examiner

*Primary Examiner* — Ruth Davis
*Assistant Examiner* — Emily Cordas
(74) *Attorney, Agent, or Firm* — Tristan A. Fuierer; Moore & Van Allen, PLLC

(57) ABSTRACT

It is provided an improved aqueous solution for the preservation of tissues and organs comprising carvedilol, tacrolimus, and trimetazidine. A synergistic effect is observed for this preservation solution which is particularly effective in marginal organs, such as steatotic livers.

11 Claims, 10 Drawing Sheets

AQUEOUS SOLUTION FOR THE PRESERVATION OF TISSUES AND ORGANS

CROSS-REFERENCE TO RELATED APPLICATIONS

This application is filed under the provisions of 35 U.S.C. §371 and claims the priority of International Patent Application No. PCT/ES2009/000267 filed on 18 May 2009 entitled "Aqueous Solution for the Preservation of Tissues and Organs" in the name of Carmen PERALTA UROZ, et al., which claims priority of Spanish Patent Application No. P200801560 filed on 19 May 2008, both of which are hereby incorporated by reference herein in their entirety.

This invention relates to an aqueous solution for preserving tissues and organs, to the use thereof, particularly, for preserving marginal organs, and to a method for preserving tissues and organs.

BACKGROUND ART

Organ transplantation is the treatment of choice for patients with end-stage chronic diseases. In spite of the advancement in the improvement of transplantation techniques, the injury of the graft occurring during the ischemic period and subsequent reperfusion is still an unresolved problem in the clinical practice.

After removal from a donor and before graft transplantation into a recipient, the organ(s) and tissues are subjected to an inherent period of ischemia. Thus, the liquid solutions used to preserve the organs and tissues have to fulfil some requirements: removal of blood from donor, fast cool down the organ, and ensure effective prevention and protection against the lesions caused by ischemia.

Static hypothermic preservation is an effective method of organ preservation during short periods of ischemia. However, prolonged ischemia periods are associated with primary graft non-function in hepatic transplantation and with graft dysfunction in renal transplantation. Additionally to the need for extending the period of ischemia, the limited pool of donors and the subsequent increase in waiting list numbers for organ transplantation have led to the acceptance of marginal organs, which tolerate poorly the injury caused by a sustained ischemia. In the case of liver transplantation, the use of marginal organs such as steatotic grafts is associated with increased risk for primary non-function or dysfunction of the graft after the transplantation, compared with non-steatotic ones. In addition, some steatotic livers are considered not suitable for transplantation, exacerbating the shortage of organs for transplantation. It is well known that most of the injury showed by a marginal organ during transplantation is related to the period of hypothermic preservation. These observations indicate that the organ preservation must be optimized. Therefore, the main aim of organ preservation is trying to prolong organ tolerance to ischemia.

There is evidence indicating that the composition of preservation solutions is a critical factor for the quality of organs kept for prolonged ischemic periods. University of Wisconsin (UW) preservation solution is considered the standard solution for liver preservation since it has proved itself effective in reducing damage caused by cold ischemia and has extended storage time limits. This preservation solution contains different components directed to enhance organ preservation including the colloid hydroxyethyl starch to prevent cell oedema, adenosine as a source of ATP on reperfusion, allopurinol and glutathione with antioxidant effects and cell membrane-impermeant agents such as lactobionic acid and raffinose. However, this preservation solution, UW, has limitations regarding the efficacy since irreversible injuries have been observed in transplanted organs when cold ischemic periods are prolonged (16 h-24 h).

Tacrolimus (TCR) is a macrolide compound with effective immunosuppressive activity, antimicrobial activity and other pharmacological activities and is of value for the prevention of rejection reactions on transplantation of organs and tissues as well as for autoimmune disorders and infectious disorders. It is known that its addition to preservation solutions can protect against reperfusion injury. A UW preservation solution containing tacrolimus has been described in the literature (K. G. Rajesh et al., "Mitochondrial Permeability transition-pore inhibition enhances functional recovery after long-time hypothermic heart preservation", *Transplantation,* 2003, vol. 76 (9), pp. 1314-20). Its action on the preservation of hearts was assayed. Nevertheless, it was concluded that tacrolimus failed to have any effect on preservation.

Carvedilol (CVD) is a lipophilic nonselective β-adrenergic blocker with vasodilator effects exerted primarily through selective a1 receptor blockade and with a strong antioxidant effect. The capacity of carvedilol to inhibit lipid peroxidation is much greater than that of other tested β-adrenergic blockers, which may explain its superior protective effects in ischemia/reperfusion models. Although the addition of antioxidants, such as carvedilol, to preservation solutions has been suggested in the literature (cf. B. Yard et al., "Prevention of cold-preservation injury of cultured endothelial cells by catecholamines andrelated compounds", *American Journal of transplantation,* 2004, vol. 4, pp. 22-30), no specific preservation solution comprising carvedilol has ever been disclosed.

A recent work indicates that the addition of trimetazidine (TMZ) to the UW preservation solution improved the capacity of this standard preservation solution to protect both in non-steatotic and, especially, in steatotic livers subjected to prolonged ischemic periods (cf. I. Ben Mosbah et al. "Trimetazidine: Is it a promising drug for use in steatotic grafts?", *World J Gastroenterol,* 2006, vol. 12(6), pp. 908-914).

Nevertheless, some of the properties of UW solution, such as high potassium concentration (required to flush the organ before graft reperfusion in the recipient) and the presence of hydroxyethyl starch (HES) as oncotic support (which could be responsible for red blood cell aggregation) do not favour the organ preservation. Recent studies have demonstrated that both liver grafts (steatotic and non-steatotic grafts) are better preserved in a modified UW preservation solution (called IGL-1), characterized by the inversion of $K^+$ and $Na^+$ concentrations and the replacement of HES by polyethylene glycol (PEG) in the original UW solution (cf. I. Ben Mosbah et al., "Preservation of steatotic livers in IGL-1 solution", *Liver Transpl,* 2006, vol. 12 (8), pp. 1215-23). On the other hand, despite the improvements offered by IGL-1 solution, the deleterious effects of ischemia-reperfusion (I/R) remain unresolved.

There is still a need of finding preservation solutions which allow prolonging organ tolerance to ischemia and minimizing the inherent risk of marginal organs subjected to transplantation.

SUMMARY OF THE INVENTION

Although preservation solutions containing tacrolimus, carvedilol, or trimetazidine are either known or suggested in the prior art, an aqueous solution for the preservation of tissues and organs comprising a combination of these three active pharmaceutical ingredients has never been suggested.

The inventors have surprisingly found that a preservation solution containing a combination of tacrolimus, carvedilol, and trimetazidine synergistically improves the preservation capacity of tissues and organs subjected to a prolonged ischemic period. Particularly, this synergistic effect is especially evident in marginal organs, such as steatotic livers, which makes the solution specially advantageous since it would improve the initial conditions of marginal organs that are available for transplantation but with deficient postsurgical results, and could increase as well the use of organs that nowadays are discarded for transplantation, and therefore to increase the amount of available organs to be transplanted.

Thus, an aspect of the present invention relates to an aqueous preservation solution for the preservation of tissues and organs comprising an effective amount of carvedilol, an effective amount of tacrolimus, and an effective amount of trimetazidine.

The aqueous preservation solution of the present invention allows maintaining tissues or organs for an amount of time that is longer than the achieved with other known preservation solutions. Another advantage of the preservation solution of the invention is that it allows lengthening the time in which a tissue or organ functions properly and in which it is useful for transplantation relative to that which would be achieved with other preservation solutions.

A second aspect of this invention relates to the use of the aqueous solution of the present invention for preserving tissues or organs. The solution can be applied on tissues or organs of mammals, including humans. Examples of said tissues are veins and arteries.

Also forms part of this invention a method for preserving tissues and organs comprising maintaining said tissues or organs in the aqueous solution of the present invention at a temperature comprised between 2-10° C. By submerging a tissue or an organ in the aqueous preservation solution of the present invention, reperfusion injury associated with tissue or organ implantation and transplant rejection is prevented.

As used herein, the phrase "an effective concentration of" an active ingredient is the amount of the active ingredient that is useful for preserving tissues or organs.

Any range value given herein may be extended or altered without losing the effects sought, as will be apparent to the skilled person. Thus, ranges given, such as concentrations, and the like, should be considered approximate, unless specifically stated.

Throughout the description and claims the word "comprise" and variations of the word, are not intended to exclude other technical features, additives, components or steps.

BRIEF DESCRIPTION OF THE DRAWINGS

The FIGS. (1-10) illustrate the effect of the addition of tacrolimus (TCR), carvedilol (CVD), and trimetazidine (TMZ) to some known preservation solutions, and the effects of the preservation solution of Example 1 (P1) when steatotic (S) and non-steatotic (NS) livers were subjected to prolonged ischemic period. In the figures, % P means percentage of protection.

DETAILED DESCRIPTION OF THE INVENTION

Figure 1:
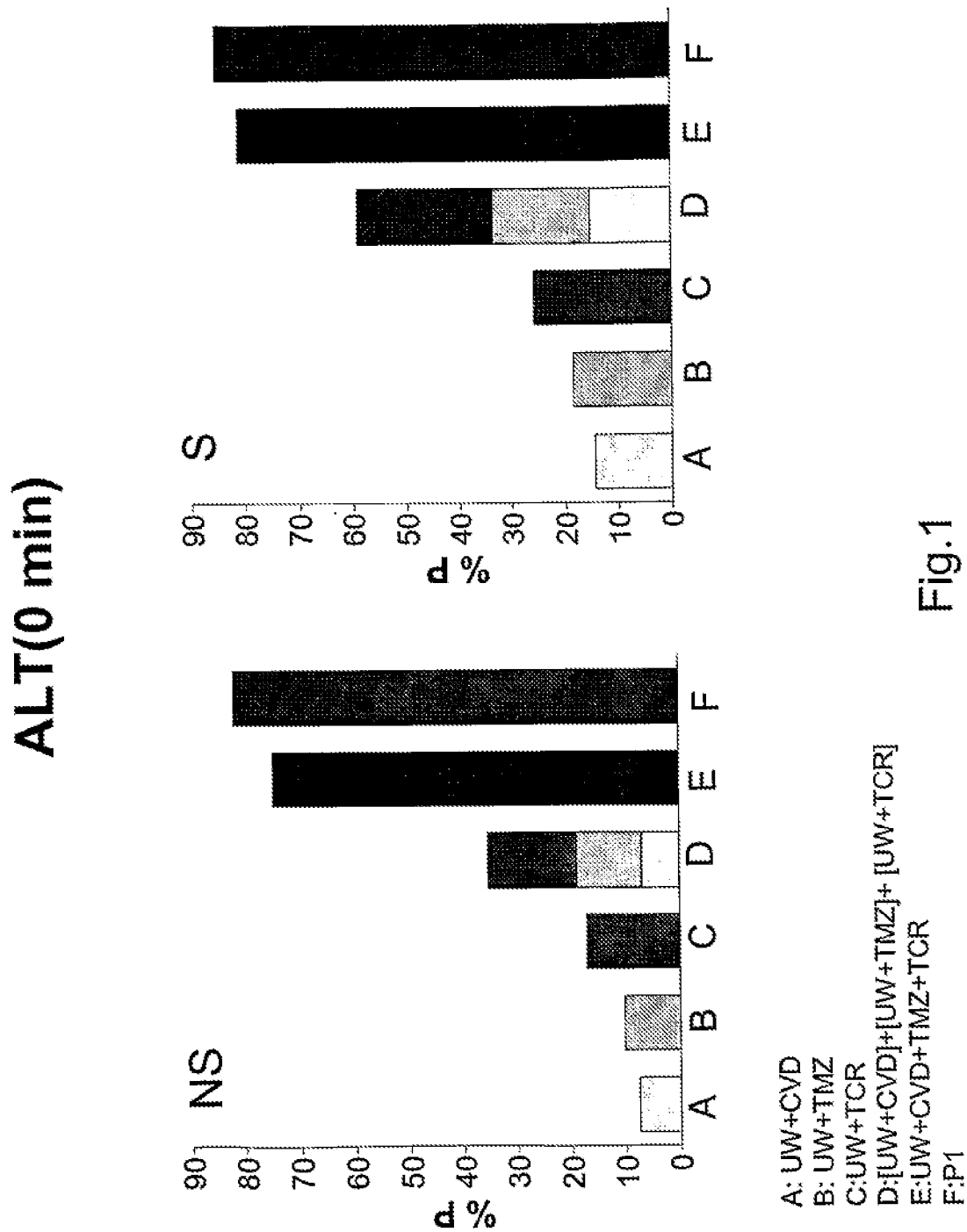
FIG. 1 illustrates the percentage of protection against UW preservation solution when the ALT values were evaluated at the end of the ischemic period (0 min).
Figure 2:
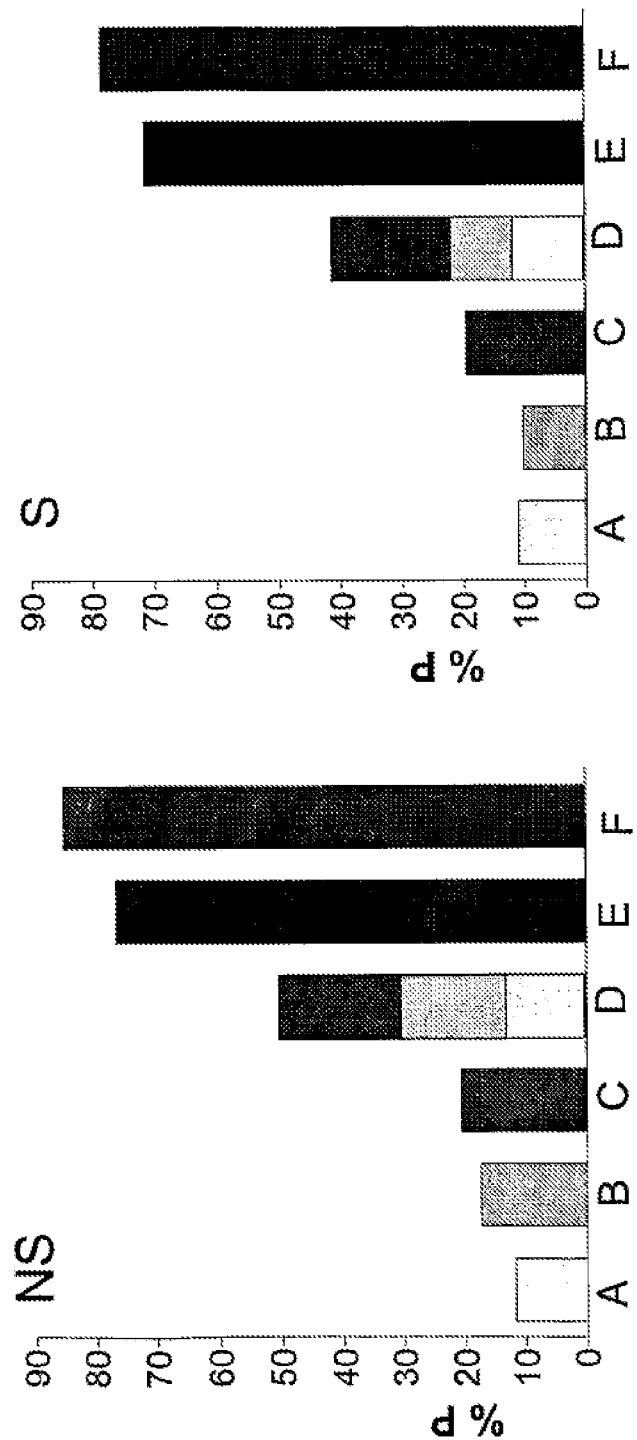
FIG. 2 illustrates the percentage of protection against UW preservation solution when the ALT values were evaluated at the end of reperfusion (120 min.).
Figure 3:
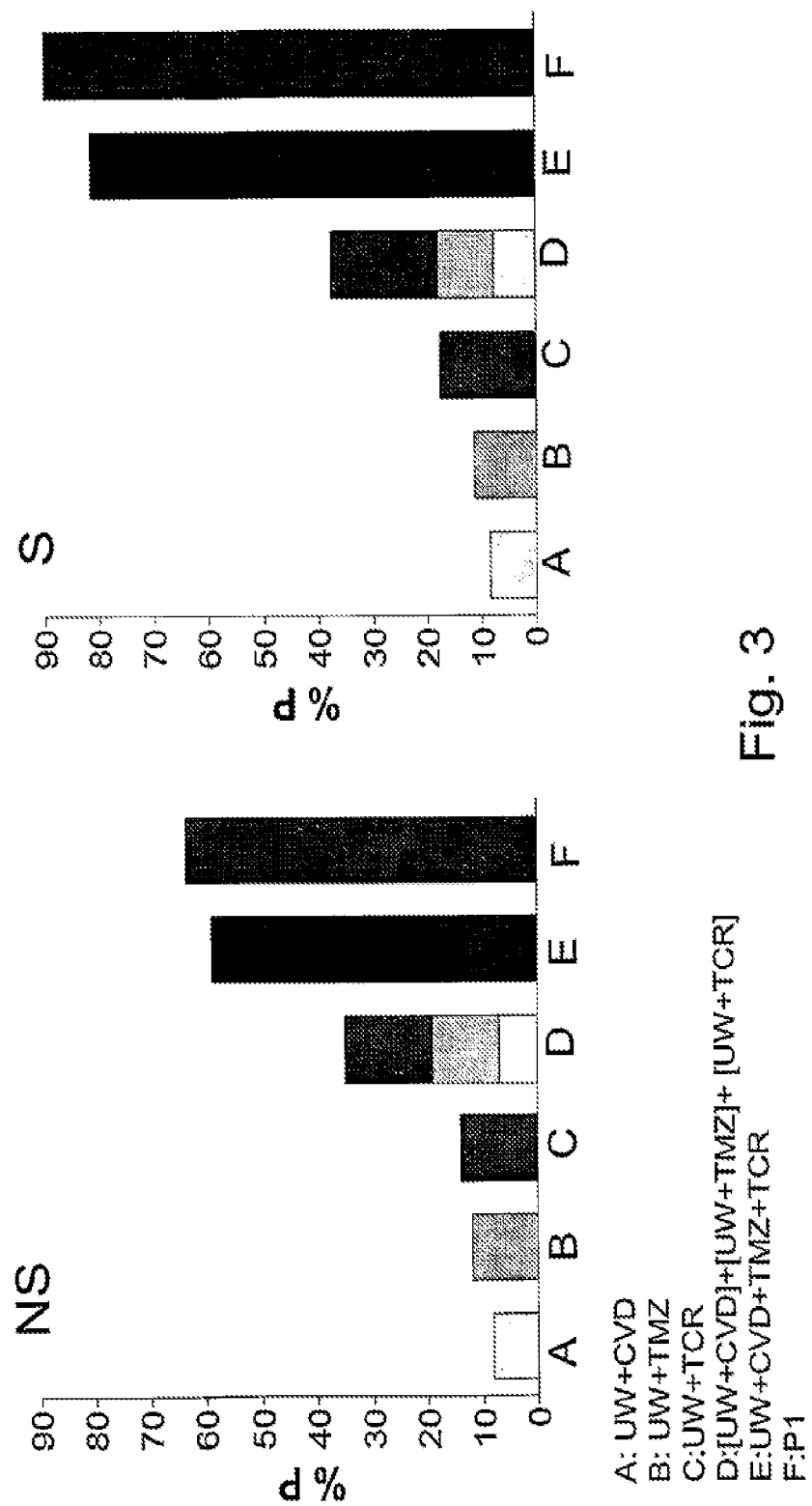
FIG. 3 illustrates the percentage of protection against UW preservation solution when the bile production was evaluated at the end of reperfusion (120 min.).
Figure 4:
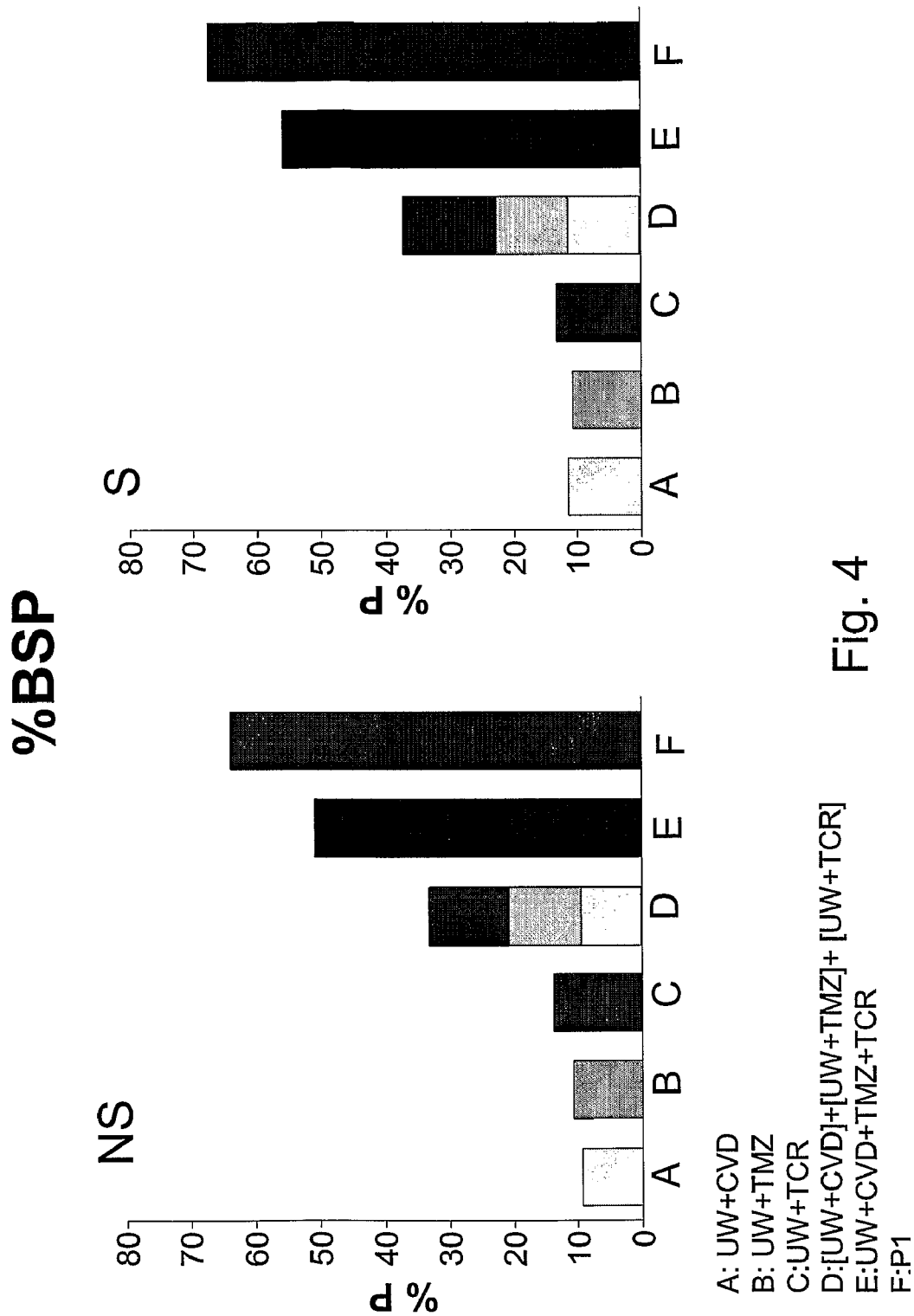
FIG. 4 illustrates the percentage of protection against UW preservation solution when the % of BSP hepatic clearance in bile was evaluated during reperfusion.
Figure 5:
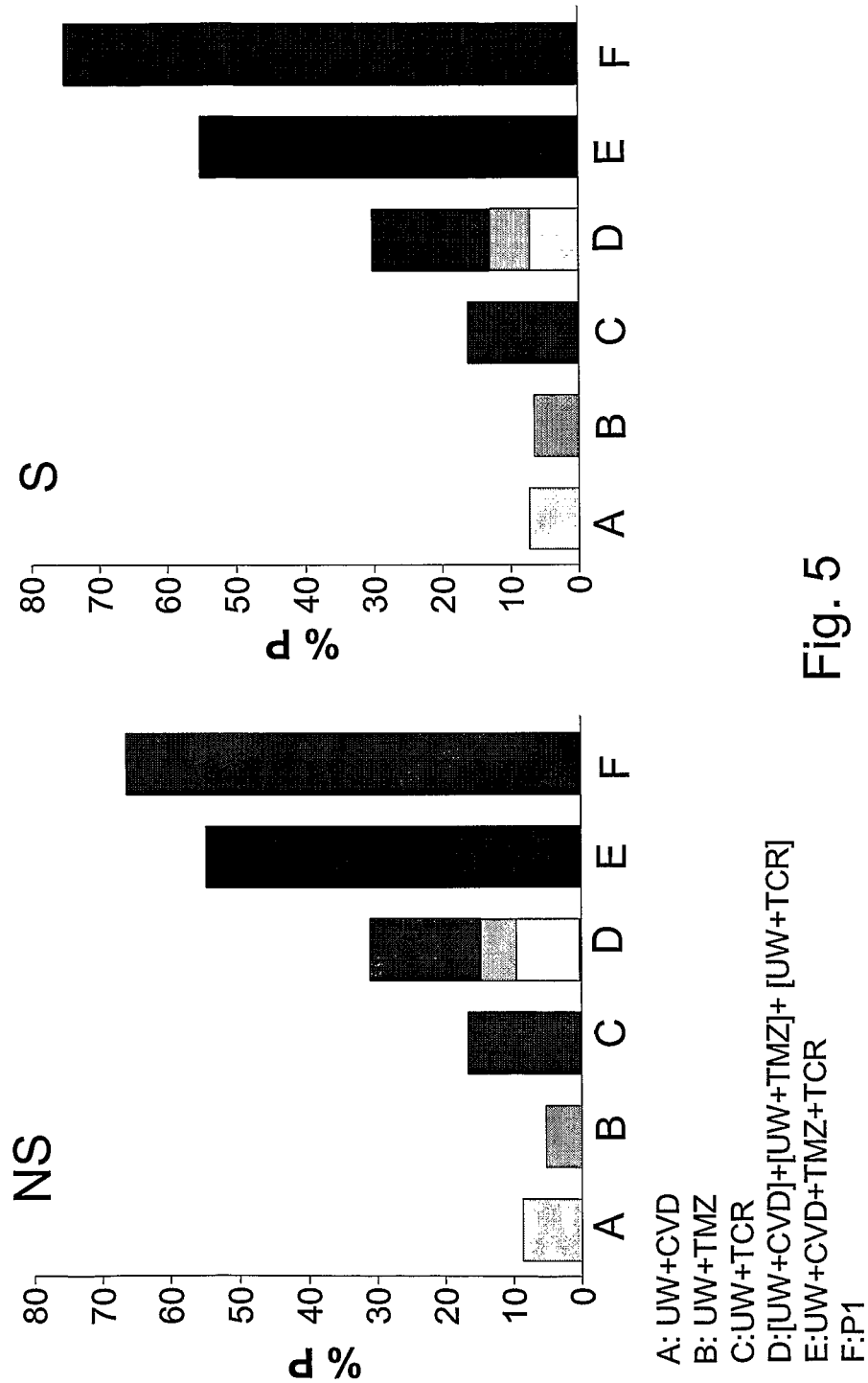
FIG. 5 illustrates the percentage of protection against UW preservation solution when the ATP levels were evaluated at the end of reperfusion (120 min.).
Figure 6:
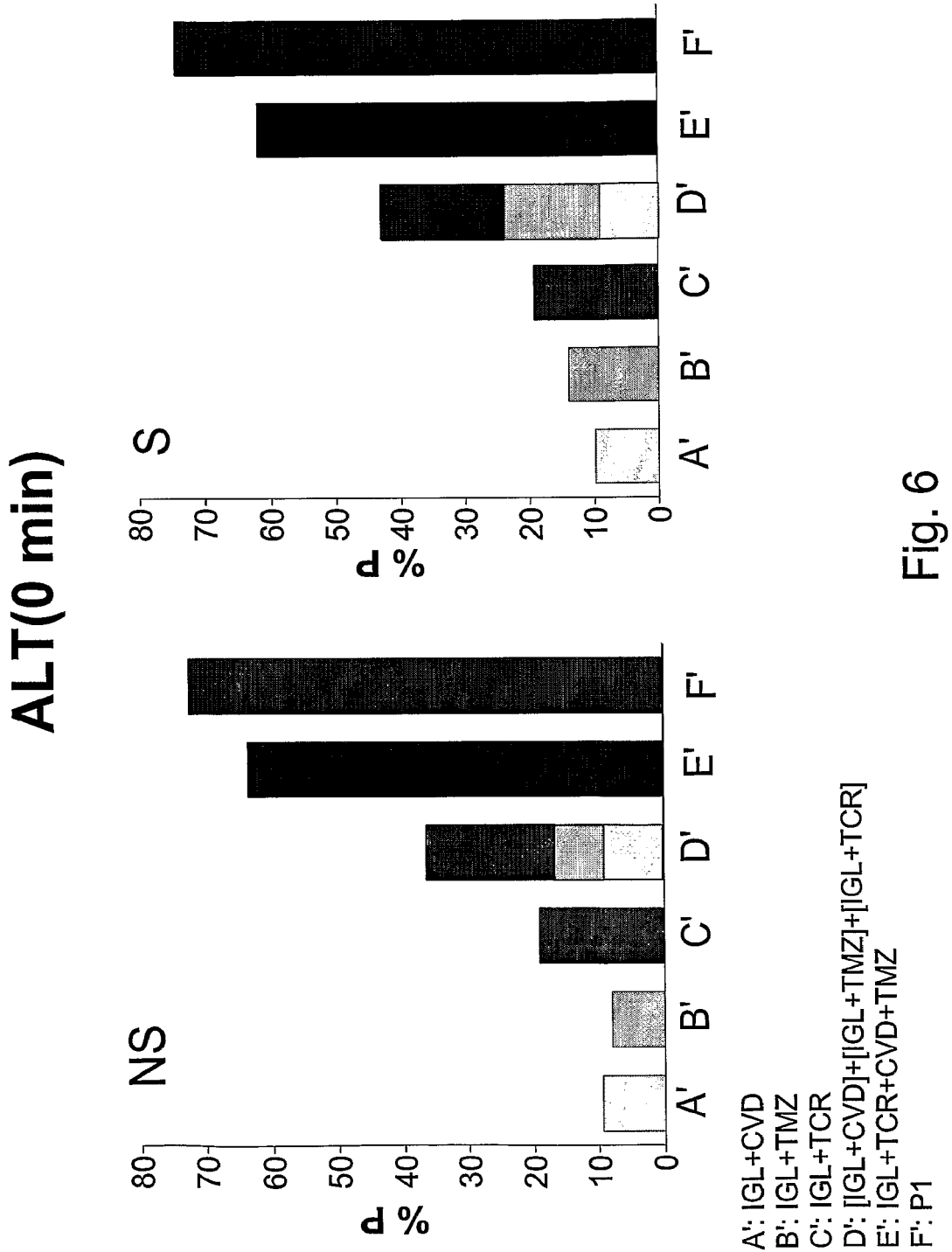
FIG. 6 illustrates the percentage of protection against IGL-1 preservation solution when the ALT values were evaluated at the end of the ischemic period (0 min.).
Figure 7:
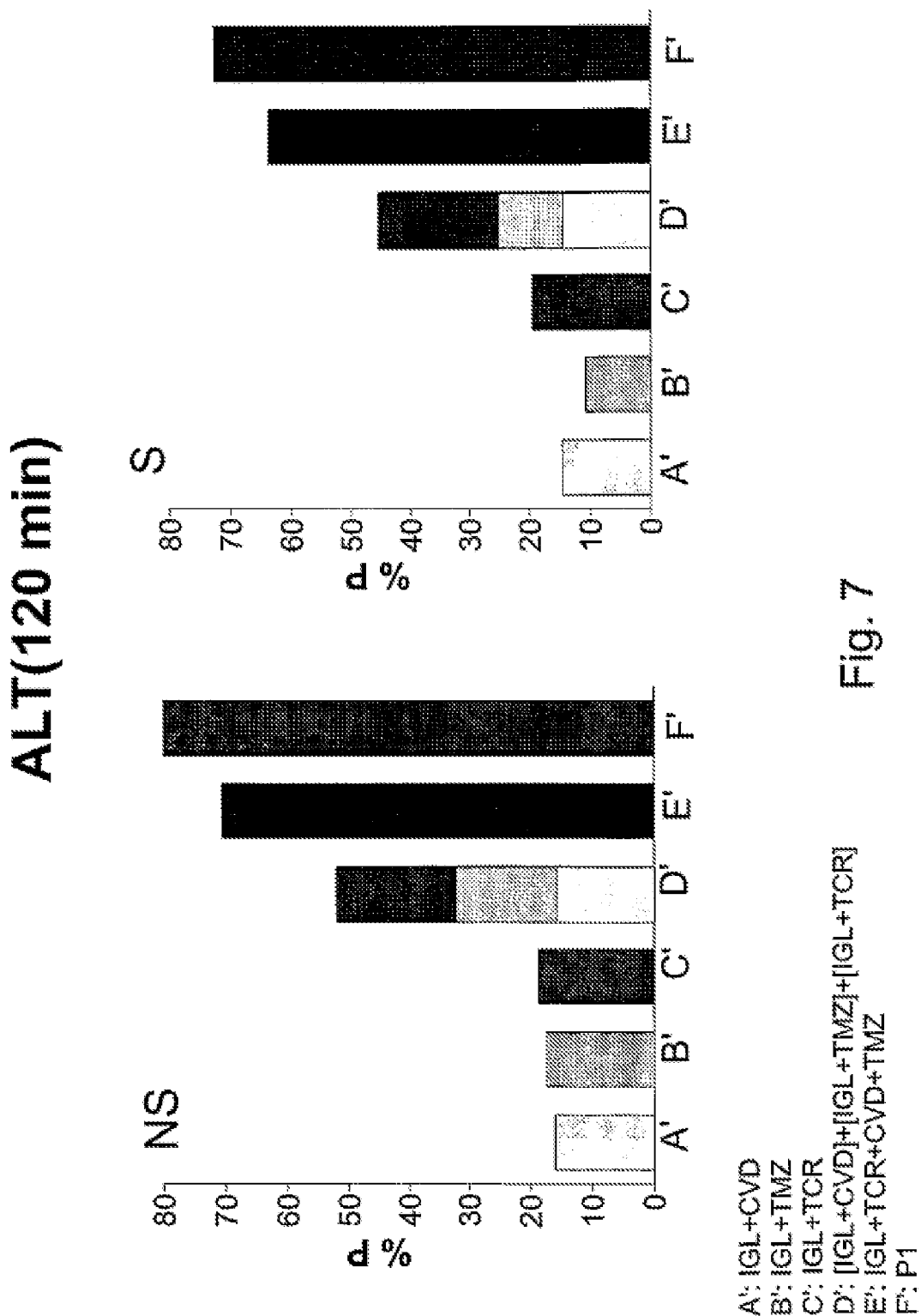
FIG. 7 illustrates the percentage of protection against IGL-1 preservation solution when the ALT values were evaluated at the end of reperfusion (120 min.).
Figure 8:
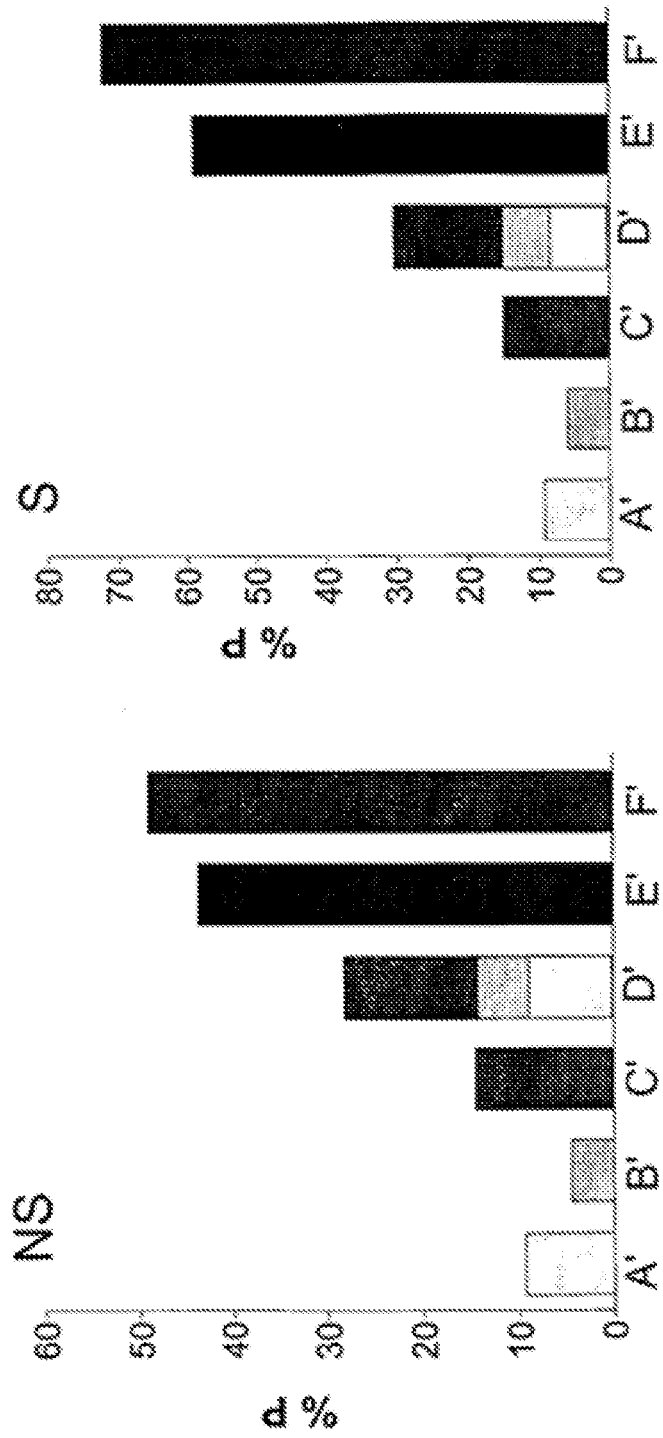
FIG. 8 illustrates the percentage of protection against IGL-1 preservation solution when the bile production was evaluated at the end of reperfusion (120 min.).
Figure 9:
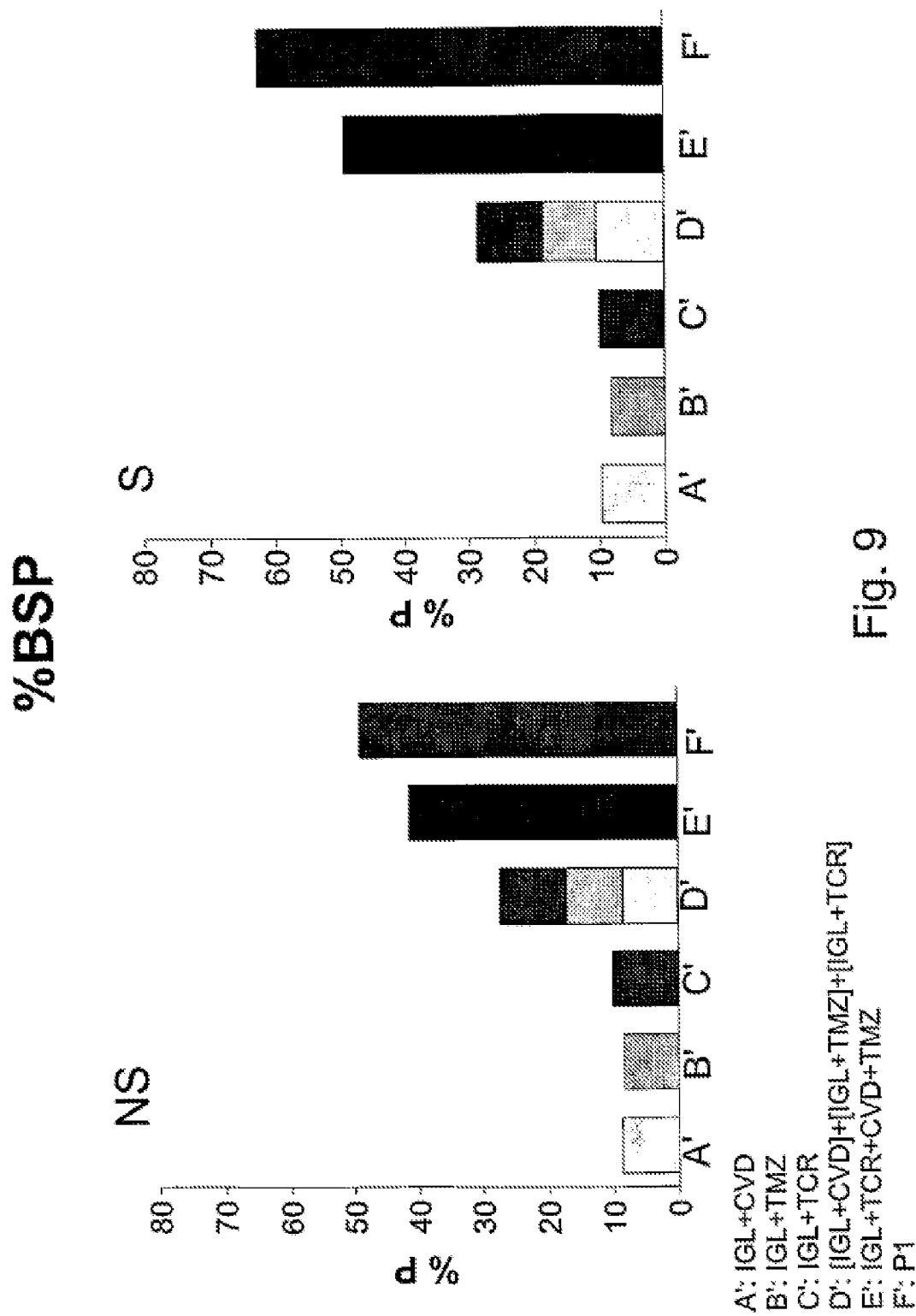
FIG. 9 illustrates the percentage of protection against IGL-1 preservation solution when the % of BSP hepatic clearance in bile was evaluated during reperfusion.
Figure 10:
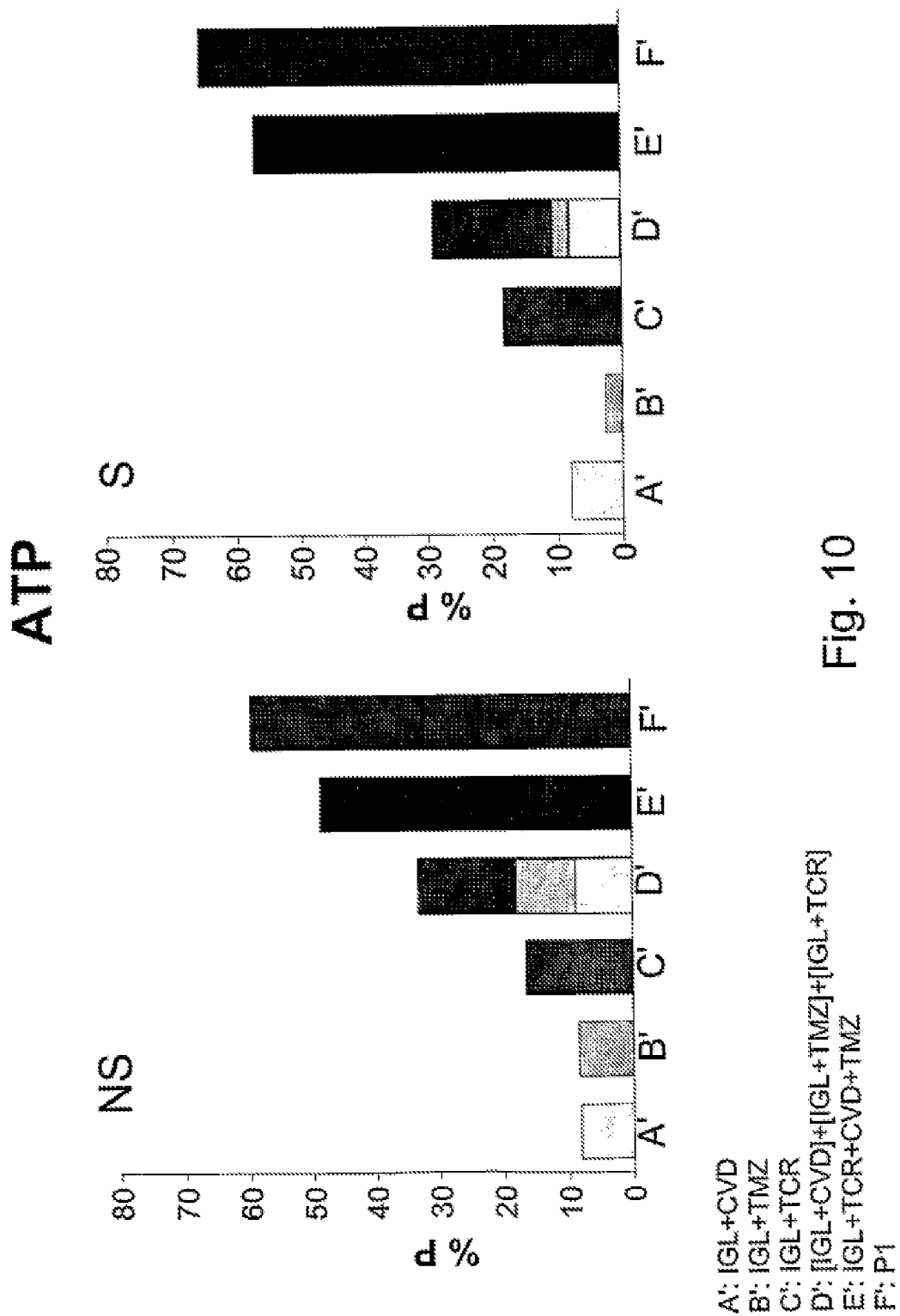
FIG. 10 illustrates the percentage of protection against IGL-1 preservation solution when the ATP levels were evaluated at the end of reperfusion (120 min.).

The aqueous solution of the present invention can be applied to tissues or organs at the time of removal from the donor, and during their storage, transportation and eventual implantation into a recipient. It can be used for short and essentially for prolonged ischemic periods.

In a preferred embodiment of the aqueous solution of the present invention, the concentration of carvedilol is from 5 to 10 microM, the concentration of tacrolimus is from 5 to 10 microM, and the concentration of trimetazidine is from 0.01 microM to 10 microM.

In order to avoid cellular and tissue oedema formation, the aqueous solution of the present invention comprises polyethylene glycol (PEG) having a molecular weight above 15.000, which allows guaranteeing the oncotic pressure. Preferably, the PEG used is a PEG of a molecular weight of 35.000. More preferably, PEG is a nonlinear purified PEG, that is to say a PEG synthesized from PEG molecules of low molecular weight.

Accordingly, in another preferred embodiment, the aqueous solution of the present invention has a pH from 6.5 to 8 and an osmolarity from 290 to 320 milimoles/kg, and further comprises PEG having a molecular weight above 15.000 in a concentration from 0.01 to 5 mM, raffinose in a concentration from 20 to 40 mM, $MgSO_4$ in a concentration from 1 to 10 mM, $H_2PO_4^-$ in a concentration from 10 to 40 mM, potassium ions in a concentration from 30 to 50 mM, sodium ions in a concentration from 110 to 160 mM, and lactobionic acid in a concentration from 70 to 140 mM.

In still another preferred embodiment the aqueous solution of the present invention has a pH of 7.4, an osmolarity of 320 milimoles/kg, and the concentration of PEG having a molecular weight above 15.000 is 0.03 mM, the concentration of raffinose is 30 mM, the concentration of $MgSO_4$ is 5 mM, the concentration of $H_2PO_4^-$ is 25 mM, the concentration of potassium ions is 40 mM, the concentration of sodium ions is 120 mM, the concentration of lactobionic acid is 100 mM, the concentration of tacrolimus is 5 microM, the concentration of carvedilol is 10 microM, and the concentration of trimetazidine is 1 microM. Preferably, PEG has a molecular weight of about 35000.

It is well known that the main cause of discarded organs to be transplanted is the steatosis. The above preferred embodiments of the preservation solution of the invention allow increasing the tolerance of steatotic livers to ischemia-reperfusion injury associated with liver transplantation. This fact allows to ameliorate the post-transplantation function of steatotic graft, and to increase the availability of suitable organs for transplantation.

A particularly preferred aqueous solution of the present invention consists of the following components:

polyethylene glycol having a molecular weight of about 35000 in a concentration of 0.03 mM, raffinose in a concentration of 30 mM, $MgSO_4$ in a concentration of 5 mM, $H_2PO_4^-$ in a concentration of 25 mM, potassium ions in a concentration of 40 mM, sodium ions in a concentration of 120 mM, lactobionic acid in a concentration of 100 mM.

tacrolimus in a concentration of 5 microM, carvedilol in a concentration of 10 microM, and trimetazidine in a concentration of 1 microM, and has a pH of 7.4 and an osmolarity of 320 milimoles/kg.

More preferably this preservation solution further comprises dexametasone in a concentration of 16 g/l, and penicillin in a concentration of 200.000 U/L.

These two preferred embodiments of the preservation solution of the invention do not contain certain drugs, such as GSH, HES, insulin, allopurinol, and adenosine, which are included in other already known preservation solutions (such as UW and/or IGL-1 preservation solutions) and which have been demonstrated to be ineffective or even to have deleterious effects on the preserved organ. A particularly relevant synergy has been observed for these preferred preservation solutions as they confer protection for both steatotic and non-steatotic livers compared with the results obtained for other preservation solutions.

As mentioned above, an additional aspect of the present invention relates to the use of the aqueous solution as described and claimed herein for preserving tissues or organs. In a preferred embodiment, the organ is an abdominal organ, such as liver, kidney, and pancreas. Preferably, the abdominal organ is a marginal organ, and more preferably is a steatotic liver.

The preservation solution of the present invention applies to static hypothermic preservation and is used at a temperature of between 2 and 10° C., preferably between 3 and 5° C., and more preferably at 4° C.

Furthermore, the present invention covers all possible combinations of particular and preferred groups described hereinabove.

Additional objects, advantages and features of the invention will become apparent to those skilled in the art in part from the description and in part from the practice of the invention. The following examples and drawings are provided by way of illustration, and are not intended to be limiting of the present invention.

EXAMPLES

Example 1

Preparation of an Aqueous Preservation Solution

An aqueous solution, whose composition is shown in Table 1, was prepared according to the process disclosed below.

TABLE 1

|  | Concentration (mM) |
| --- | --- |
| Lactobionic acid | 100 |
| $H_2PO_4^-$ | 25 |
| $MgSO_4$ | 5 |
| Raffinose | 30 |
| PEG 35000 | 0.03 |
| Potassium ions | 40 |
| Sodium ions | 120 |
| Tacrolimus | $5 \cdot 10^{-3}$ |
| Carvedilol | $10 \cdot 10^{-3}$ |
| Trimetazidine | $1 \cdot 10^{-3}$ |

Step 1:
To a solution containing 1 g of dialysed polyethylene glycol (PEG 35.000), 4.11 mg of tacrolimus (TCR) were added and stirred to form a first solution.

Step 2:
35.83 g of lactobionic acid were added into a one litre receptacle containing 800 ml of water (distilled and deionized) at room temperature and stirred until dissolved. Then, 0.60 g of $MgSO_4$, 22.5 mL of 5N NaOH, 6 mL of 5N KOH, 3.4 g of $KH_2PO_4$, and 17.83 g of raffinose were added to form a second solution. Subsequently, 1 mL of a solution containing TMZ from a stock solution (stock solution: 2.66 mg of TMZ dissolved in 10 ml of water) and 10 ml of CVD from a stock solution (stock solution: 6.5 mg of carvedilol in 8 ml of tartaric acid and 8 ml of water) were added to this second solution.

The solution prepared in step 1 was mixed with the solution prepared in step 2, and then 5 N NaOH was added as needed to adjust the pH to 7.4±0.1.

Finally, water was added to the receptacle to bring volume up to 1 liter, and then the solution was filtered, and sterilised. A solution having an osmolarity of 320±10 mOsm/L was obtained. Prior to use, dexamethasone (16 g/L) and penicillin (200,000 U/L) were added.

Example 2

In this example, the effect of the aqueous solution of the present invention on the liver in relation to the effect obtained when UW and IGL-1 preservation solutions were used was compared.

Hepatic injury and function were evaluated by measuring transaminases, bile production, hepatic clearance (% BSP) and ATP content.

To carry out the study, homozygous (obese, Ob) and heterozygous (lean, Ln) Zucker rats, aged 16-18 weeks, purchased from Iffa-Credo (L'Abresle, France), were used. An isolated perfused liver was used to evaluate hepatic injury and function, without the influence of other organs, plasma constituents and neuronal/hormonal effects. Hepatic architecture, microcirculation and bile production are preserved in this experimental model. This experimental model used has been considered in the literature as appropriated for testing the effectiveness of different preservation solutions for transplantation. All procedures were performed under isoflurane inhalation anaesthesia. The study respected European Union regulations (Directive 86/609/CEE) for animal experiments.

Liver Procurement and Experimental Groups

The surgical technique was performed as described in previous studies (I. Ben Mosbah, et al. "Preservation of steatotic livers in IGL-1 solution", *Liver Transpl* 2006, vol. 12 (8), pp. 1215-23, and I. Ben Mosbah et al. "Addition of adenosine monophosphate-activated protein kinase activators to University of Wisconsin solution: a way of protecting rat steatotic livers", *Liver Transpl.*, 2007, vol. 13(3), pp. 410-25). After cannulation of the common bile duct, the portal vein was isolated and the splenic and pyloric branches were ligated. All animals were randomly distributed into the following experimental groups as described below.

Preservation Solutions and Experimental Groups

The composition of UW, IGL-1 and P1 preservation solutions is shown in Table 2, being P1 a preservation solution according to the present invention.

TABLE 2

| Components | Properties | UW | IGL-1 | P1 |
|---|---|---|---|---|
| $Na^+$ (mmol) | Cation | 30 | 100 | 120 |
| $K^+$ (mmol) | Cation | 100 | 30 | 40 |
| $Mg^{2+}$ (mmol) | Cation | 5 | 5 | 5 |
| Sulphate (mmol) | Buffer | 5 | 5 | 5 |
| Phosphate (mmol) | Buffer | 25 | 25 | 25 |
| Lactobionic acid (mmol) | Buffer | 100 | 100 | 100 |
| Raffinose (mmol) | Sugar | 30 | 30 | 30 |
| HES (g/l) | Colloid | 50 | — | — |
| PEG (g/l) | Colloid | — | 1 | 1 |
| Adenosine (mmol) | Energy source | 5 | 5 | — |
| Allopurinol (mmol) | Antioxidant | 1 | 1 | — |
| GSH (mmol) | Antioxidant | 3 | 3 | — |
| Trimetazidine (μmol) | Mitochondrial protector | — | — | 1 |
| Carvedilol (μmol) | Antioxidant | — | — | 10 |
| Tacrolimus (μmol) | Anti-inflammatory | — | — | 5 |
| Insulin (U/L) | Mitochondrial Protector | 40 | 40 | — |
| Dexamethasone (g/L) | Membrane Protector | 16 | 16 | 16 |
| Penicillin (U/L) | Antibiotic | 200.000 | 200.000 | 200.000 |

HES = hydroxyethyl starch;
GSH = Glutathione.

A) Study I: P1 vs. UW solution

1) UW: Livers from 16 Zucker rats (8 Ln and 8 Ob) were preserved for 24 h at 4° C. in UW solution.
2) UW+CVD: Livers from 16 Zucker rats (8 Ln and 8 Ob) were preserved for 24 h at 4° C. in UW solution containing 10 μM of carvedilol.
3) UW+TMZ: Livers from 16 Zucker rats (8 Ln and 8 Ob) were preserved for 24 h at 4° C. in UW solution containing 1 μM of trimetazidine.
4) UW+TCR: Livers from 16 Zucker rats (8 Ln and 8 Ob) were preserved for 24 h at 4° C. in UW solution containing 5 μM of tacrolimus.
5) UW+CVD+TMZ+TCR: Livers from 16 Zucker rats (8 Ln and 8 Ob) were preserved for 24 h at 4° C. in UW solution containing 10 μM of carvedilol, 1 μM of trimetazidine, and 5 μM of tacrolimus.

The results obtained in groups 1-5 were compared with those obtained when livers from 16 Zucker rats (8 Ln and 8 Ob) were preserved for 24 h at 4° C. in P1 preservation solution.

B) Study II: P1 vs. IGL-1

1) IGL: Livers from 16 Zucker rats (8 Ln and 8 Ob) were preserved for 24 h at 4° C. in IGL-1 solution.
2) IGL+CVD: Livers from 16 Zucker rats (8 Ln and 8 Ob) were preserved for 24 h at 4° C. in IGL-1 solution containing 10 μM of carvedilol.
3) IGL+TMZ: Livers from 16 Zucker rats (8 Ln and 80b) were preserved for 24 h at 4° C. in IGL-1 solution containing 1 μM of trimetazidine.
4) IGL+TCR: Livers from 16 Zucker rats (8 Ln and 8 Ob) were preserved for 24 h at 4° C. in IGL-1 solution containing 5 μM of tacrolimus.
5) IGL+CVD+TMZ+TCR: Livers from 16 Zucker rats (8 Ln and 8 Ob) were preserved for 24 h at 4° C. in IGL-1 solution containing 10 μM of carvedilol, 1 μM of trimetazidine, and 5 μM of tacrolimus.

The results obtained in groups 1 to 5 were compared with those obtained when livers from 16 Zucker rats (8 Ln and 8 Ob) were preserved for 24 h at 4° C. in P1 preservation solution.

Procedure

After 24 h of cold preservation of the graft, the levels of cumulative alanine aminotransferase (ALT) after prolonged ischemia were measured. In addition, after 24 h of cold preservation of the graft, and in order to mimic the warm ischemic period suffered by the graft during surgical implantation into the recipient, livers were exposed at 22° C. for 30 min. Livers were then connected via the portal vein to a recirculating perfusion system and were perfused for 120 min at 37° C. During the first 15 min of perfusion, the flow was progressively increased in order to stabilize the portal pressure at 12 mm Hg (Pression Monitor BP-1, Instruments, Inc, Sarasota, Fla., USA). The flow was controlled using a peristaltic pump (Minipuls 3, Gilson, France). The perfusion liquid consisted of a cell culture medium (William's medium E, Bio Whitaker, Spain) with the Krebs-Heinseleit—albumin solution. The perfusion liquid was oxygenated with 95% $O_2$ and 5% $CO_2$ gas mixture and the temperature of the perfusion liquid was maintained at 37° C. At the end of normothermic reperfusion (120 min) aliquots of the perfusion liquid were collected to evaluate ALT. Bile production and hepatic clearance (% BSP) in bile samples and the content of ATP in liver samples, were also evaluated.

Biochemical Determinations

Transaminase assay. Transaminases were evaluated as a parameter of hepatic injury according to the instructions provided by commercial kits from Boehringer Mannheim (Munich, Germany).

Bile production. Bile production was assessed as a parameter of liver function. Bile was collected through the bile duct and bile production was estimated by measuring the bile volume obtained after 120 min perfusion and reported as μl/g liver.

BSP hepatic clearance. As with bile production, BSP hepatic clearance is considered as another reliable parameter of hepatic function. 10 mg of BSP (bromosulfophthalein) were added to the perfusion liquid thirty minutes after starting perfusion. The concentration of BSP in bile samples was determined by measuring the absorbance at 580 nm. BSP hepatic clearance was expressed as % BSP.

ATP. Liver samples were homogenized in a solution containing perchloric acid, and ATP levels were measured by high-performance liquid chromatography.

Statistical Study

Data were expressed as mean value±standard error of the mean. Data obtained were submitted to a statistical study by an analysis of variance test, and the level of statistical significance was determined by the Student-Newman-Keuls test. In all cases, the results were considered significantly different when p<0.05.

The levels of ALT were assessed to predict the hepatic injury after the graft preservation period. This measure is a valuable tool for predicting organ damage after cold preservation. At the end of cold ischemia, higher levels of transaminases were observed in steatotic livers compared to non-steatotic livers preserved either in UW or in IGL solutions. This confirms the poor tolerance of steatotic livers to the damaging effects caused during cold ischemia.

The values of ALT (U/L) at the end of cold ischemia for grafts preserved in UW solution were 32.87±2.91 and 152.23±2.21 for non-steatotic and steatotic livers, respectively. The values of ALT (U/L) at the end of cold ischemia for grafts preserved in IGL solution were 21.44±0.62 and 87.47±3.20 for non-steatotic and steatotic livers, respectively.

Higher transaminase levels were observed in steatotic livers at the end of reperfusion compared with those found in non-steatotic livers. The values of ALT (U/L) at the end of reperfusion for grafts preserved in UW preservation solution were 45.05±3.53 and 159.11±3.01 for non-steatotic and steatotic livers, respectively. The values of ALT (U/L) at the end of reperfusion for grafts preserved in IGL preservation solution were 35.62±2.32 and 121.41±1.23 for non-steatotic and steatotic livers, respectively.

Liver function was assessed by measuring bile production and hepatic clearance (% BSP). Bile production and % BSP were lower in steatotic livers preserved either in UW or in IGL solutions than in non-steatotic livers. The values of bile production (μl/g/120 min) at the end of reperfusion for livers preserved in UW solution were 9.55±0.25 and 1.46±0.18 for non-steatotic and steatotic livers, respectively. The values of bile production (μl/g/120 min) at the end of reperfusion for livers preserved in IGL solution were 14.25±0.63 and 3.44±0.38 for non-steatotic and steatotic livers, respectively. The values of % BSP in bile at the end of reperfusion for livers preserved in UW solution were 6.13±1.13 and 4.70±0.65 for non-steatotic and steatotic livers, respectively. The values of % BSP in bile at the end of reperfusion for livers preserved in IGL solution were 8.04±0.61 and 7.34±0.58 for non-steatotic and steatotic livers, respectively.

Lower ATP levels at the end of reperfusion were observed in steatotic livers preserved either in UW or in IGL-1 solutions than those recorded for non-steatotic livers. The values of ATP (μM/g) at the end of reperfusion for livers preserved in UW solution were 0.90±0.02 and 0.61±0.03 for non-steatotic and steatotic livers, respectively. The values of ATP (μM/g) at the end of reperfusion for livers preserved in IGL solution were 1.19±0.09 and 0.77±0.06 for non-steatotic and steatotic livers, respectively.

Tables 3-6 below show the effect of the addition of tacrolimus (TCR), carvedilol (CVD), and trimetazidine (TMZ) to known preservation solutions, and the effect of the preservation solution of Example 1 (P1) when steatotic and non-steatotic livers were subjected to prolonged ischemic period. Values are expressed as percentage of protection against UW or IGL-1 preservation solutions of injury and hepatic functionality parameters: ALT at the end of 24 h of ischemia (0 min), ALT at the end of 120 min of reperfusion (120 min.), bile production, % BSP, and ATP content at the end of reperfusion (120 min.).

TABLE 3

Non-steatotic livers (from Zucker rats Ln) in UW preservation solution

|  | UW + CVD | UW + TMZ | UW + TCR | [UW + CVD] + [UW + TMZ] + [UW + TCR] | UW + TCR + CVD + TMZ | P1 |
|---|---|---|---|---|---|---|
| ALT (0 min.) | 7.51 | 10.10 | 17.16 | 34.77 | 74.90 | 82.10 |
| ALT (120 min.) | 11.66 | 17.44 | 20.59 | 49.69 | 76.68 | 85.05 |
| Bile | 8.24 | 12.0 | 14.0 | 34.24 | 58.87 | 63.37 |
| % BSP | 9.38 | 10.69 | 13.76 | 33.83 | 50.80 | 63.76 |
| ATP | 8.65 | 5.28 | 16.66 | 30.59 | 54.8 | 66.37 |

TABLE 4

Steatotic livers (from Zucker rats Ob) in UW preservation solution

|  | UW + CVD | UW + TMZ | UW + TCR | [UW + CVD] + [UW + TMZ] + [UW + TCR] | UW + TCR + CVD + TMZ | P1 |
|---|---|---|---|---|---|---|
| ALT (0 min.) | 14.44 | 18.54 | 25.77 | 58.75 | 81.06 | 85.20 |
| ALT (120 min.) | 11.0 | 10.12 | 19.55 | 40.67 | 71.33 | 78.53 |
| Bile | 8.50 | 11.40 | 17.60 | 37.50 | 81.40 | 91.50 |
| % BSP | 11.45 | 10.70 | 13.30 | 35.45 | 56.0 | 67.50 |
| ATP | 7.26 | 6.53 | 16.22 | 30.01 | 55.20 | 75.0 |

TABLE 5

Non-steatotic livers (from Zucker rats Ln) in IGL-1 preservation solution

|  | IGL + CVD | IGL + TMZ | IGL + TCR | [IGL + CVD] + [IGL + TMZ] + [IGL + TCR] | IGL + TCR + CVD + TMZ | P1 |
|---|---|---|---|---|---|---|
| ALT (0 min.) | 9.42 | 7.98 | 19.17 | 36.57 | 63.71 | 72.57 |
| ALT (120 min.) | 15.97 | 17.41 | 18.59 | 51.97 | 70.52 | 81.11 |
| Bile | 9.26 | 4.50 | 14.52 | 28.28 | 43.70 | 49.0 |
| % BSP | 8.74 | 8.37 | 10.15 | 27.26 | 41.40 | 49.0 |
| ATP | 8.17 | 8.41 | 16.56 | 33.14 | 48.63 | 59.60 |

TABLE 6

Steatotic livers (from Zucker rats Ob) in IGL-1 preservation solution

|  | IGL + CVD | IGL + TMZ | IGL + TCR | [IGL + CVD] + [IGL + TMZ] + [IGL + TCR] | IGL + TCR + CVD + TMZ | P1 |
|---|---|---|---|---|---|---|
| ALT (0 min.) | 9.89 | 13.94 | 19.24 | 43.07 | 61.75 | 74.27 |
| ALT (120 min.) | 14.62 | 10.75 | 19.47 | 44.84 | 63.76 | 72.69 |

TABLE 6-continued

Steatotic livers (from Zucker rats Ob) in IGL-1 preservation solution

|  | IGL + CVD | IGL + TMZ | IGL + TCR | [IGL + CVD] + [IGL + TMZ] + [IGL + TCR] | IGL + TCR + CVD + TMZ | P1 |
| --- | --- | --- | --- | --- | --- | --- |
| Bile | 9.30 | 6.0 | 15.0 | 30.30 | 59.0 | 72.10 |
| % BSP | 9.73 | 8.22 | 9.98 | 27.93 | 49.28 | 62.58 |
| ATP | 7.99 | 2.63 | 18.15 | 28.77 | 57.0 | 65.37 |

According to the hepatic injury and functionality parameters, our results indicate that the combined addition of tacrolimus, carvedilol and trimetazidine, to UW or IGL-1 preservation solutions (UW+TCR+CVD+TMZ or IGL-1+TCR+CVD+TMZ) resulted in higher degree of protection for steatotic and non-steatotic livers compared with the results obtained when tacrolimus, carvedilol and trimetazidine were added, separately to UW (i.e. [UW+TCR]+[UW+CVD]+[UW+TMZ]) or IGL-1 (i.e. [IGL+TCR]+[IGL+CVD]+[IGL+TMZ]) preservation solution. Moreover, the preservation solution P1 conferred a higher degree of protection for both steatotic and nonsteatotic livers compared with the results obtained for UW+TCR+CVD+TMZ and IGL-1+TCR+CVD+TMZ.

Summarizing, from results showed in Tables 3-6, it can be stated that a synergistic effect is observed for the solutions of the present invention, which is particularly evident for P1 preservation solution. This synergistic effect is especially improved in steatotic livers.

The invention claimed is:

1. An aqueous solution for the preservation of tissues and organs comprising a concentration of carvedilol comprised between 5 and 10 microM, a concentration of tacrolimus comprised between 5 and 10 microM, and a concentration of trimetazidine comprised between 0.01 microM and 10 microM.

2. The solution according to claim 1, having a pH from 6.5 to 8 and an osmolarity from 290 to 320 milimoles/kg and further comprising:
polyethylene glycol having a molecular weight above 15,000 Da in a concentration from 0.01 to 5 mM,
raffinose in a concentration from 20 to 40 mM,
$MgSO_4$ in a concentration from 1 to 10 mM,
$H_2PO_4^-$ in a concentration from 10 to 40 mM,
potassium ions in a concentration from 30 to 50 mM,
sodium ions in a concentration from 110 to 160 mM, and
lactobionic acid in a concentration from 70 to 140 mM.

3. The solution according to claim 2, wherein the pH is 7.4, the osmolarity is 320 milimoles/kg, the concentration of polyethylene glycol is 0.03 mM, the concentration of raffinose is 30 mM, the concentration of $MgSO_4$ is 5 mM, the concentration of $H_2PO_4^-$ is 25 mM, the concentration of potassium ions is 40 mM, the concentration of sodium ions is 120 mM, the concentration of lactobionic acid is 100 mM, the concentration of tacrolimus is 5 microM, the concentration of carvedilol is 10 microM, and the concentration of trimetazidine is 1 microM.

4. The solution according to claim 3, consisting of:
polyethylene glycol having a molecular weight of about 35,000 Da in a concentration of 0.03 mM,
raffinose in a concentration of 30 mM,
$MgSO_4$ in a concentration of 5 mM,
$H_2PO_4^-$ in a concentration of 25 mM,
potassium ions in a concentration of 40 mM,
sodium ions in a concentration of 120 mM,
lactobionic acid in a concentration of 100 mM,
tacrolimus in a concentration of 5 microM,
carvedilol in a concentration of 10 microM, and
trimetazidine in a concentration of 1 microM.

5. The solution according to claim 3, further comprising dexamethasone in a concentration of 16 g/l, and penicillin in a concentration of 200,000 U/L.

6. The solution according to claim 1 further comprising polyethylene glycol having a molecular weight above 15,000 Da.

7. The solution according to claim 1 characterized in that it does not contain GSH, HES, insulin, allopurinol and adenosine.

8. A method for preserving tissues and organs comprising maintaining said tissues or organs in the aqueous preservation solution as defined in claim 1 at a temperature comprised between 2-10° C.

9. The method according to claim 8, wherein the organ is an abdominal organ.

10. The method according to claim 9, wherein the abdominal organ is a marginal organ.

11. The method according to claim 10, wherein the marginal organ is a steatotic liver.

* * * * *